US009782351B2

(12) United States Patent
Gill et al.

(10) Patent No.: US 9,782,351 B2
(45) Date of Patent: Oct. 10, 2017

(54) IMMUNOMODULATION USING SPORES AND POLLEN GRAINS

(71) Applicant: Texas Tech University System, Lubbock, TX (US)

(72) Inventors: Harvinder S. Gill, Lubbock, TX (US); Shashwati Atwe, Lubbock, TX (US); Yunzhe Ma, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 18 days.

(21) Appl. No.: 14/053,091

(22) Filed: Oct. 14, 2013

(65) Prior Publication Data

US 2014/0105961 A1    Apr. 17, 2014

Related U.S. Application Data

(60) Provisional application No. 61/713,708, filed on Oct. 15, 2012, provisional application No. 61/857,488, filed on Jul. 23, 2013.

(51) Int. Cl.
| | |
|---|---|
| *A61K 9/16* | (2006.01) |
| *A61K 39/00* | (2006.01) |
| *A61K 39/07* | (2006.01) |
| *A61K 39/12* | (2006.01) |
| *A61K 39/39* | (2006.01) |

(52) U.S. Cl.
CPC .............. *A61K 9/167* (2013.01); *A61K 39/00* (2013.01); *A61K 39/07* (2013.01); *A61K 39/12* (2013.01); *A61K 39/39* (2013.01); *A61K 2039/542* (2013.01); *A61K 2039/55588* (2013.01); *C12N 2740/16034* (2013.01)

(58) Field of Classification Search
None
See application file for complete search history.

(56) References Cited

U.S. PATENT DOCUMENTS

| | | |
|---|---|---|
| 5,013,552 A | 5/1991 | Samir Amer et al. |
| 5,275,819 A | 1/1994 | Amer et al. |
| 5,800,821 A | 9/1998 | Acheson et al. |
| 7,087,236 B1 | 8/2006 | Brayden |
| 7,608,270 B2 | 10/2009 | Beckett et al. |
| 7,846,654 B2 | 12/2010 | Atkin et al. |

FOREIGN PATENT DOCUMENTS

| | | | | |
|---|---|---|---|---|
| WO | 0200232 A2 | 1/2002 | | |
| WO | 03055513 A2 | 7/2003 | | |
| WO | WO 2005/000280 | * 1/2005 | ............... | A61K 9/50 |
| WO | WO 2009/077749 | * 6/2009 | ............... | A61K 9/50 |
| WO | 2011160026 A2 | 12/2011 | | |

OTHER PUBLICATIONS

Gut et al. 'Mechanism of Inhibition of Bacillus anthracis Spore Outgrowth by the Lantibiotic Nisin.' ACS Chem Biol. 6(7):744-752, 2011.*
Black et al. J. Aller. Clin. Immuno.. 10(2):156-158, 1939.*
Howlett et al. J. Cell. Sci. 13:603-619, 1973.*
Kuby Immunology, 4th Edition, Chapter 18, "Vaccines," pp. 449-465 (2001).*
Mukherjee et al. 'Allergic Asthma: Influence of Genetic and Environmental Factors.' J. Biol. Chem. 286(38):32883-32889, 2011.*
Kurucz et al. 'Current Animal Models of Bronchial Asthma.' Curr. Pharm. Des. 12:3175-3194, 2006.*
Vajdy, M., et al. "Cholera toxin adjuvant promotes long-term immunological memory in the gut mucosa to unrelated immunogens after oral immunization." Immunology (1992) 75(3): 488-492.
Snider, D. P., et al. "Production of IgE antibody and allergic sensitization of intestinal and peripheral tissues after oral immunization with protein Ag and cholera toxin." J Immunol (May 4, 1994) 153(2): 647-657.
Marinaro, M., et al. "Mucosal adjuvant effect of cholera toxin in mice results from induction of T helper 2 (Th2) cells and IL-4." J Immunol (Nov. 15, 1995) 155(10): 4621-4629. (Abstract).
Xu-Amano, J., et al. "Helper T cell subsets for immunoglobulin A responses: oral immunization with tetanus toxoid and cholera toxin as adjuvant selectively induces Th2 cells in mucosa associated tissues." J Exp Med (Oct. 1, 1993) 178(4): 1309-1320.
Summerton, N. A., et al. "Toward the development of a stable, freeze-dried formulation of Helicobacter pylori killed whole cell vaccine adjuvanted with a novel mutant of *Escherichia coli* heat-labile toxin." Vaccine (Feb. 3, 2010) 28 (5): 1404-1411.
Kirkpatrick, B. D., et al. "The novel oral typhoid vaccine M01ZH09 is well tolerated and highly immunogenic in 2 vaccine presentations." J Infect Dis (Jun. 30, 2005) 192(3): 360-366.
Tacket, C. O., et al. "Phase 2 clinical trial of attenuated *Salmonella enterica* serovar typhi oral live vector vaccine CVD 908-htrA in U.S. volunteers." Infect Immun (Mar. 2000) 68(3): 1196-1201.
Bishop, A. L., et al. "Vibrio cholerae: lessons for mucosal vaccine design." Expert Rev Vaccines (Jan. 2011) 10 (1): 79-94.
Jiang, G., et al. "Anthrax vaccine powder formulations for nasal mucosal delivery." Journal of Pharmaceutical Sciences (Jan. 2006) 95(1): 80-96.
International Search Report (KIPO) PCT/US2013/064832 dated Jan. 8, 2014.
Third Party Observation [PCT/US2013/064832] Hamad, Shwan A. et al., "Encapsulation of living cells into sporopollenin microcapsules," J. Mater. Chem. 2011, 21, 18018.

(Continued)

*Primary Examiner* — Nora Rooney
(74) *Attorney, Agent, or Firm* — Edwin S. Flores; Daniel J. Chalker; Chalker Flores, LLP

(57) ABSTRACT

The present invention includes compositions, methods of making and using the compositions for modulating the immune response in a subject by providing a vaccine composition having a pollen/spore disposed in a pharmaceutical carrier for delivery to a subject, wherein the pollen/spore comprises multiple pores that connect an outer surface of the pollen/spore to an inner cavity and one or more antigens disposed on the outer surface, in the inner cavity, in the multiple pores, or a combination thereof, wherein the one or more antigens modulate an immune responses in the subject.

32 Claims, 7 Drawing Sheets

(56) References Cited

OTHER PUBLICATIONS

Atwe Shashwati U et al: "Pollen grains for oral vaccination", Journal of Controlled Release, Elsevier, Amsterdam, NL, vol. 194, Aug. 23, 2014 (Aug. 23, 2014), pp. 45-52.
Ball, David A. et al: "Structure of the exosporjum and sublayers of spores of the Bacillus cereus family revealed by electron crystal lography", Molecular Microbiology., vol. 68, No. 4, May 1, 2008 (May 1, 2008), pp. 947-958.
Duc L H et al: "Bacterial Spores As Vaccine Vehicles", Infection and Immunity, American Society for Microbiology, US, vol. 71, No. 5, May 1, 2003 (May 1, 2003), pp. 2810-2818.
Zhou et al: "Oral administration of a Bacillus subtilis spore-based vaccine expressing Clonorchis sinensis tegumental protein 22.3kDa confers protection against Clonorchis sinensis", Vaccine, Elsevier LTD, GB, vol. 26, No. 15, Feb. 20, 2008 (Feb. 20, 2008), pp. 1817-1825.
Extended European Search Report [Ep 13846840.0] dated Jul. 8, 2016.

\* cited by examiner

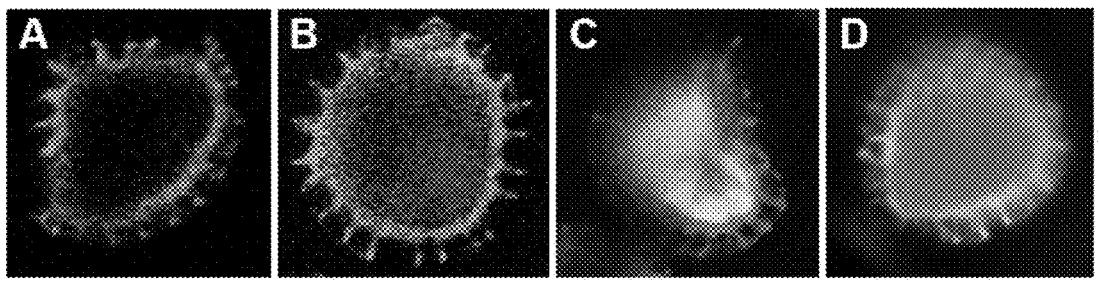
FIGURES 3A | FIGURE 3B | FIGURE 3C | FIGURE 3D
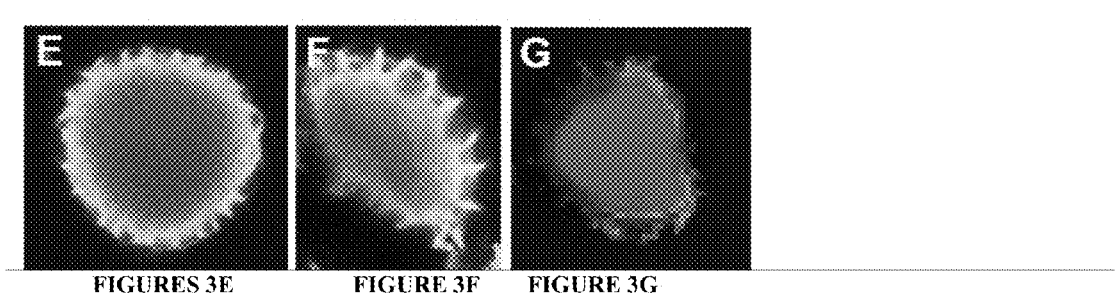
FIGURES 3E | FIGURE 3F | FIGURE 3G
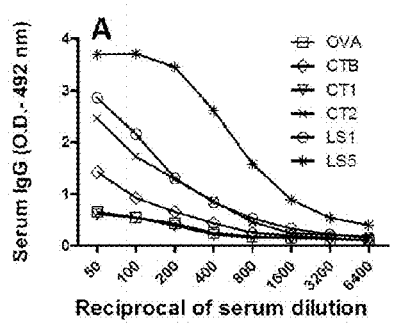
FIGURE 4A
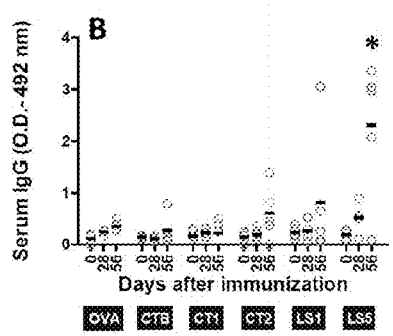
FIGURE 4B
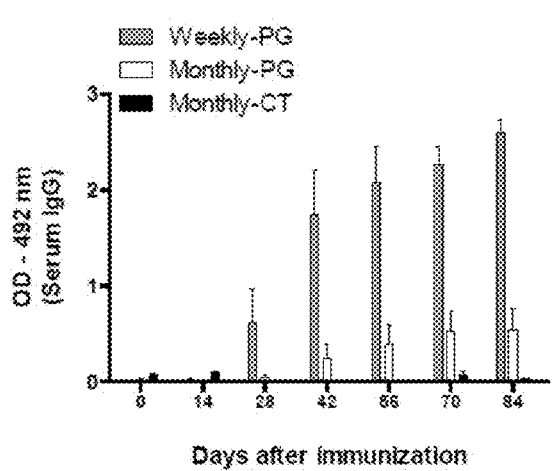
FIGURE 5

IMMUNOMODULATION USING SPORES AND POLLEN GRAINS

CROSS-REFERENCE TO RELATED APPLICATIONS

This Non-Provisional Patent Application claims priority to U.S. Provisional Patent Application Ser. No. 61/857,488, filed Jul. 23, 2013 and U.S. Provisional Patent Application Ser. No. 61/713,708, filed Oct. 15, 2012, the contents of each of which is incorporated by reference herein in its entirety.

TECHNICAL FIELD OF THE INVENTION

The present invention relates generally to methods, compositions and formulations in which an agent is loaded into a microsphere, and more specifically to a drug or other active agent loaded into the interstices or pores of a natural microsphere, e.g., a pollen grain or a spore.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with vaccinations. Vaccinations are an effective and cost-efficient means of protecting against infectious agents; however, injecting vaccines using a hypodermic needle is not the most convenient, likable, or safe method of vaccination. The use of hypodermic needles results in significant pain and discomfort to patients, requires trained personnel for administration, and can cause accidental needle-pricks resulting in transmission of blood borne pathogens such as HIV and hepatitis virus. In contrast, oral administration of vaccination is painless, is the most convenient to use, and can result in high patient compliance. It also has the potential to allow self-administration of vaccines and can allow rapid distribution of vaccines to the public in case of pandemics. Furthermore, processing of locally delivered antigens in the gut-associated lymphoid tissues (GALT) can induce strong mucosal immunity in the gut and other distant mucosal surfaces. On the other hand, the systemic delivery of vaccines using hypodermic needles is a poor stimulator of mucosal immunity. Mucosal immunity is important because mucosal surfaces such as the gut-lining and the respiratory epithelium form a major portal of entry for pathogens, and neutralization of pathogens on mucosal surfaces can form a first line of defense. Thus, overall the oral route of a vaccination is not only safer, convenient and painless, but it is also expected to be functionally superior due to the potential of stimulating both the systemic and the mucosal arms of immunity.

Pollen grains have served as delivery vehicles for their naturally-contained genetic material and allergenic proteins throughout the ages and are natural delivery devices for macromolecules the size of proteins and nucleic acids, as well as for smaller molecules. Their surfaces adhere to tissue surfaces and particularly to mucous membranes and remain in contact for prolonged periods of time to release the substances contained therein to the blood stream or circulatory system. For example, U.S. Pat. No. 7,608,270, entitled, "Dosage Form," discloses a pharmaceutical or dietetic dosage form comprising of effective quantity of an active substance chemically or physically bound to support comprising sporopollenin, or other similar exine coating of spores, of a plant or fungus, optionally with further excipients.

For example, U.S. Pat. No. 7,846,654, entitled, "Uses of Sporopollenin" discloses the use of an exine shell of a naturally occurring spore, or a fragment thereof, as an antioxidant, for instance in a composition or formulation containing an active substance. Also provided is a method for reducing rancidity, or other oxidative degradation, of a substance, composition, or formulation, by encapsulating the substance, composition, or formulation in, or chemically binding it to, or mixing it with, an exine shell of a naturally occurring spore or a fragment thereof. These patents achieved significant removal of plant native proteins not seen in earlier studies and specify that the pollen grain shell must have protein content less than 0.5% of the exine coating. Based on this qualification the inventors of patent 'a' and 'b' were able to have new patents issued.

For example, U.S. Pat. No. 5,013,552, entitled, "Modified Pollen Grains for Delivering Biologically Active Substances to Plants and Animals," discloses loaded pollen grains, which are suitable for use as delivery systems for introducing biologically active substances into or on plants and animals. Such pollen grains are suitable to deliver both small and large (macromolecules) molecules. Preferred pollen grains are those that have been defatted and then pre-treated to be free of antigenic materials and that have special surface features that facilitate their attachment to tissue surfaces, particularly to mucous membranes. The most preferred pollen grains are those that have spiny or irregular or fragmented surfaces. Also disclosed are a method of pre-treating the pollen grains to remove antigenic materials; a method of loading the pollen grains with the biologically active material; and a method of incorporating such pre-treated, loaded pollen grains into formulations or dosage forms suitable for introduction into or on a plant or animal body.

For example, U.S. Pat. No. 5,275,819, entitled, "Drug loaded pollen grains with an outer coating for pulsed delivery," discloses a pulsating release composition comprising natural microspheres, such as pollen grains or spores, into which are loaded a biologically active that is subsequently releasable therefrom in a predetermined location in or on a plant or animal in a series (generally 3 or more) of pulses. The composition comprises a group of substantially similar loaded microspheres coated with multiple barrier layers alternating with multiple active substance layers in a concentric onion-like structure, the barrier layers being slowly soluble to delay release of active substance from the underlying layer thereof until after the pulse of active substance provided by the overlying layer has subsided. In another preferred embodiment, the composition comprises a plurality of loaded microspheres divided into as many fractions as the desired number of pulses, the loaded microspheres in each consecutive fraction being coated with a barrier layer adapted to dissolve consecutively more slowly to delay release of active substance from such fraction until after the pulse of active substance provided by the prior fraction of consecutively more soluble barrier-coated microspheres has subsided. In another aspect of the invention, the active substance-containing bodies in the compositions may be coated with one or a mixture of absorption-promoting enzymes.

SUMMARY OF THE INVENTION

The present invention provides a method of modulating the immune response in a subject by providing a composition comprising a pollen/spore disposed in a pharmaceutical carrier for delivery to a subject, wherein the pollen/spore comprises multiple pores that connect an outer surface of the pollen/spore to an inner cavity and one or more antigens disposed on the outer surface, in the inner cavity, in the multiple pores, or a combination thereof, wherein the one or more antigens modulate an immune responses in the subject; and administering the composition to the subject to modulate an immune responses. The modulation includes an increase or a decrease in the immune response towards the antigen or to modulate allergies or abnormal immune responses including auto-immunity. The one or more antigens correspond are against infectious agents, toxins, cancer, and various auto immune diseases and include oligonucleotides, proteins, peptides, deoxyribonucleic acid (DNA), ribonucleic acid (RNA), cells (broken or intact), lipids, toxin variants, carbohydrates, virus-like particles, liposomes, live attenuated or killed natural or recombinant microorganisms, bacteria, viruses, and particulate vaccine delivery systems, virosomes, polymeric/inorganic/organic micro and nanoparticles, immune stimulating complexes (ISCOMS) and combinations thereof. The vaccine composition may be delivered orally, nasally, through pulmonary route, through rectal route, through eyes, through skin, through ears, through vaginal route, through injection into various tissues or into blood by any means and may be a liquid, a solid, an aerosolized form or a combination thereof. The composition may further include a cryoprotectant selected from trehalose or other sugars/carbohydrates. The one or more antigens are deposited, physically attached, bound, adsorbed, chemically linked or a combination thereof. The composition may further include a polymer coating applied to the pollen/spore, wherein the polymer coating is a diffusion barrier, a coating that includes physical or chemical adsorption/attachment/anchoring points, plugs one or more of the multiple pores, coats the inner cavity, or a combination thereof and may include anchoring points that are polymeric/inorganic/organic macro, micro and nanoparticles or films.

The present invention provides a vaccine to modulate an immune response in the subject composition comprising a pollen/spore disposed in a pharmaceutical carrier for delivery to a subject, wherein the pollen/spore comprises multiple pores connecting an outer surface to an inner cavity of the pollen/spore and one or more antigens disposed on the outer surface, in the inner cavity, in the multiple pores, or a combination thereof, wherein the one or more antigens modulate an immune responses in the subject. The vaccine may include a polymer coating applied to the pollen/spore, wherein the polymer coating is a diffusion barrier, a coating that includes physical or chemical adsorption/attachment/anchoring points, plugs one or more of the multiple pores, coats the inner cavity, or a combination thereof.

The present invention provides a pollen/spore to modulate an immune responses in the subject composition comprising an outer pollen/spore surface; an inner pollen/spore cavity; multiple pores connecting the outer pollen/spore surface and the inner pollen/spore cavity; one or more antigens disposed on the outer pollen/spore surface, in the inner pollen/spore cavity, about the multiple pores, wherein the one or more antigens modulate an immune responses in the subject.

The present invention also includes a method of modulating the immune response in a subject comprising the steps of: providing a composition comprising one or more antigens and at least one of an intact or fragment of a pollen or pollen spore in an amount sufficient to trigger an immune response disposed in a pharmaceutical carrier for delivery to the subject, wherein the pollen/pollen spore comprises multiple pores; and administering the composition to the subject to modulate an immune responses. In one aspect, the antigen is selected from at least one of bacteria, viruses, fungi, protozoans, parasites, prions, toxins, cancer, allergies, and various auto-immune diseases. In another aspect, the one or more antigens comprise oligonucleotides, proteins, peptides, deoxyribonucleic acid (DNA), ribonucleic acid (RNA), cells (broken or intact), lipids, toxin variants, carbohydrates, virus-like particles, liposomes, live attenuated or killed natural or recombinant microorganisms, bacteria, viruses, and particulate vaccine delivery systems, liposomes, virosomes, polymeric/inorganic/organic micro and nanoparticles, immune stimulating complexes (ISCOMS) and combinations thereof, wherein antigens are in composition or can be attached/adsorbed/anchored physically or chemically to pollen/spore at the exterior surface, interior surface/cavity or pores. In another aspect, the composition is delivered orally, nasally, through pulmonary route, through rectal route, through eyes, through skin or its appendages, through ears, through vaginal route, through injection into various tissues or into blood. In another aspect, the method further comprises the step of providing the subject with one or more compositions that neutralize gastric acid selected from at least one of before, during or after immunization. In another aspect, the composition is provided without neutralizing gastric acid selected from at least one of before, during or after immunization. In another aspect, the composition activates Natural Killer cell response. In another aspect, the composition activates an antigen-specific Natural Killer cell response. In another aspect, the composition activates one or more immune responses. In another aspect, the composition activates one or more immune responses selected from at least one of B cell, T cell, an adaptive immune response, or an innate immune response.

The present invention also includes a composition comprising an intact or fragment of pollen/spore disposed in a pharmaceutical carrier for delivery to a subject and an antigen, wherein the pollen/spore comprises multiple pores to modulate an immune response against the antigen. In one aspect, modulation comprises an increase or a decrease in the immune response. In another aspect, the modulation is towards infectious agents including bacteria, viruses, fungi, protozoans, parasites, prions, toxins, cancer, allergies, and various auto-immune diseases.

BRIEF DESCRIPTION OF THE DRAWINGS

For a more complete understanding of the features and advantages of the present invention, reference is now made to the detailed description of the invention along with the accompanying figures and in which:

FIG. 1A is a SEM image of *Lycopodium clavatum* (clubmoss) spores (technically *lycopodium* pollens are called spores), FIG. 1B is a SEM image of *Alnus glutinosa* (alder black), FIG. 1C is a SEM image of *Artemisia vulgaris* (mugwort), and FIG. 1D is a SEM image of *Helianthus annuus* (sunflower).

FIG. 2A is a SEM image of the surface morphology, FIG. 2B is a SEM image of a manually cracked spore before treatment showing biological matter inside (white arrows), and FIG. 2C is a SEM image of a manually cracked spore after treatment showing clean interior.

FIGS. 3A-3G are confocal micrographs of filled *lycopodium* spores. FIG. 3A is an image of unfilled spores, FIG. 3B is an image of spores filled with sulforhodamine (558 Da), FIG. 3C is an image of spores filled with dextran conjugated to fluorescein isothiocyanate (4000 Da), FIG. 3D is an image of spores filled with ovalbumin conjugated to texas red (45,000 Da), FIG. 3E is an image of spores filled with bovine serum albumin conjugated to texas red (67,000 Da), FIG. 3F is an image of spores filled with recombinant protective antigen of anthrax conjugated to Alexa Fluor 555 (83,000 Da), and FIG. 3G is an image of spores filled with dextran conjugated to fluorescein isothiocyanate (2000,000 Da).

FIGS. 4A and 4B are graphs of OVA specific IgG antibody response in mice serum. FIG. 4A is a graph of a titration curve for pooled day 56 serum. FIG. 4B is a graph of IgG antibody in 1:200 diluted serum of individual mice of a group.

FIG. 5 is a graph of Anti-OVA IgG levels in serum.

FIG. 6 is a graph of Anti-OVA IgA levels in saliva.

FIG. 7 is a graph of Anti-OVA IgA levels in vaginal wash.

FIGS. 8A and 8B are transmission electron micrographs (TEMs) of *lycopodium* spores with gold nanoparticles. FIG. 8A is a TEM image of the Section of a single spore, and FIG. 8B is a TEM image of the Zoom-in of a portion of the spore.

FIG. 9 is a transmission electron micrograph of a sectioned *lycopodium* spore.

FIGS. 10A-10C are scanning electron micrographs (SEMs) transmission electron micrographs (TEMs) and Energy-dispersive X-ray spectroscopy (EDX) images of a *lycopodium* spore. FIG. 10A is an SEM of a *lycopodium* spore containing aluminum hydroxide particles, FIG. 10B is an EDX spectrum of the inside of the *lycopodium* spore containing aluminum hydroxide, and FIG. 10C is a TEM of *lycopodium* spore containing iron oxide particles.

FIG. 11 is a photograph of *lycopodium* spores containing iron oxide microparticles being magnetically held on the side of a plastic tube.

FIGS. 12A-12C show the effects of gastric acid on the systemic immune response (IgG) in serum. FIG. 12A shows a titration curve of pooled serum, FIG. 12B shows IgG in individual animal serum samples at each time point (days 0, 28, and 56)(dilution 1:400 chosen from the titration curve), and FIG. 12C shows IgG subtypes in the day 56 pooled serum samples (dilution 1:400)(*** stands for $P<0.001$ of that group compared to the OVA and OVA-Na).

FIGS. 13A-13C show the effects of neutralization of gastric acid on the systemic immune response (IgG) in serum. FIG. 13A shows a titration curve of pooled serum, FIG. 13B shows IgG in individual animal serum samples at each time point (days 0, 21, 42, and 63)(dilution 1:100 chosen from the titration curve), and FIG. 13C shows IgG subtypes in the day 63 pooled serum samples (dilution 1:400)(** stands for $P<0.0079$ of that group with respect to all others at the same timepoint).

FIG. 14 shows the mucosal immune response (IgA) in fecal droppings: IgA in individual animal fecal extracts at each time point (days 0, 28, and 56)(dilution 1:5)(* stands for a $P<0.001$, and  stands for $P<0.01$).

FIGS. 15A-15C show the systemic immune response (IgG) in serum after 6 months: FIG. 15A shows a titration curve of pooled serum, FIG. 15B shows IgG in individual animal serum samples (dilution 1:400))(*** stands for $P<0.001$ and * stand for $P<0.05$ of that group with respect to the OVA and OVA-Na), and FIG. 15C shows IgG subtypes in pooled serum samples (dilution 1:400).

FIGS. 16A and 16B show that the novel pollen-based vaccines of the present invention induce Ag-specific NK cell memory and antibody-dependent cell-mediated cytotoxicity (ADCC). FIG. 16A shows the response of Balb/c mice (n=5/group) primed on day 0 and boosted on day 28 with 100 μg OVA (OVA), or with LS(5 mg)-OVA(100 μg) (LS-OVA) through oral gavage. Seven months later, animals were challenged with respective formulations through oral gavage, and organs were harvested for analysis 6 days later. 500 CFSE labeled autologous B cells were either left naïve (background killing), or loaded with 5 μg/ml OVA or 4 μg/ml gp41, as indicated, and co-cultured for 6 h with 5,000 sorted NK cells, and NK:B cell ratios were assessed by flow cytometry, and FIG. 16B shows the response of Balb/c mice (n=3/group) that were primed on day 0, and boosted on day 28 with 100 μg gp41 of HIV (gp41) or with 5 mg LS (5 mg)-gp41(100 μg) (LS-gp41) through oral gavage. At 1 month post-boost, animals were challenged with respective formulations, and 11 days later organs were harvested for analysis. Lamp-1 expression on NK cells was assessed by flow cytometry after a 6 h coculture of autologous B cells, incubated with 5 μg/ml OVA or 4 μg/ml gp41, with equal numbers of sorted hepatic NK cells in the presence of 2 μg/ml Ab specific to Lamp-1a. (Vac: vaccination). Ag: antigen, Ab: antibody, APC: antigen presenting cell, LS: *lycopodium* spore, Lamp-1: Lysosomal-associated membrane protein 1.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes vaccines for use in both active and passive immunization embodiments. Immunogenic compositions, proposed to be suitable for use as a vaccine, may be prepared most readily directly from immunogenic (or antigenic) proteins and/or peptides prepared in a manner disclosed herein.

As used herein, composition that neutralize gastric acid may include, but are not limited to $H_2$ antagonists that indirectly decrease gastric acid production (e.g., cimetidine, burimamide, metiamide, ranitidine, or omeprazole), or even antacids that neutralize existing acid, such as sodium bicarbonate, calcium bicarbonate, potassium bicarbonate, or drugs such as Gaviscon, dried aluminum hydroxide-magnesium carbonate gels.

The present invention provides compositions that include pollen grains and plant spores for oral vaccination. Oral vaccination is needle-free, child-friendly, convenient, painless, amenable to self-administration, and is safer because it eliminates needle stick injuries and eliminates sharp medical waste. However, degradation of vaccine antigens in the acid and enzyme-rich environment of the stomach, and poor uptake of vaccine molecules across the tightly juxtaposed epithelial cells of the intestinal mucosa continue to hinder the use of the oral route of vaccination. We cleaned the spores of *lycopodium clavatum* (commonly called club moss), formulated the clean spores with ovalbumin (OVA) as a model protein vaccine and fed to mice with this formulation. The present invention provides formulations with a very strong immune response against OVA as measured via OVA-specific immunoglobulin G (IgG) in mouse blood. This immune response was found to be even superior to that when mice were fed cholera toxin with OVA. Cholera toxin is a potent but toxic oral adjuvant and is routinely used as a 'standard' to evaluate new vaccine delivery systems and formulations.

Figure 1A:
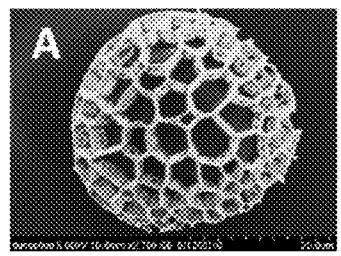
FIGS. 1A-1D are scanning electron micrographs (SEMs) of different pollen species.
Figure 1B:
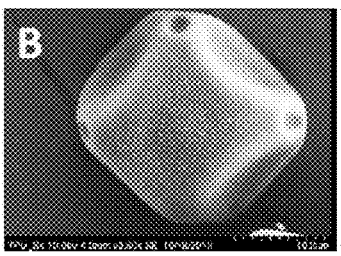
Figure 1C:
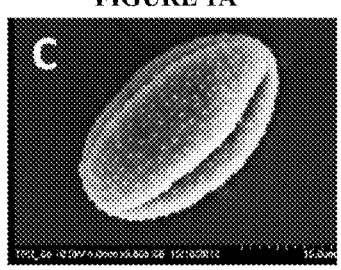
Figure 1D:
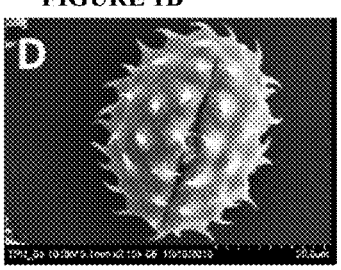

FIGS. 1A-1D are scanning electron micrographs of different pollen species. FIG. 1A is a SEM image of *Lycopodium clavatum* (clubmoss) spores (technically *lycopodium* pollens are called spores), FIG. 1B is a SEM image of *Alnusglutinosa* (alder black), FIG. 1C is a SEM image of *Artemisia vulgaris* (mugwort), and FIG. 1D is a SEM image of *Helianthus annuus* (sunflower).

Generally, antigen and molecules used for immunization or vaccination experience a highly degradative environment in the stomach and the tightly packed epithelial cells lining the intestinal mucosa offer high resistance to their transport into the body. To overcome these delivery challenges, live attenuated or recombinant microorganisms such as bacteria and viruses, and particulate vaccine delivery systems such as liposomes, virosomes, polymeric micro and nanoparticles, and immune stimulating complexes (ISCOMS) have been examined. Various techniques that seek to target microfold (M) cells to enable higher antigen uptake through endocytosis have also been tested. Toxins such as cholera toxin (CT) and heat labile enterotoxin (LT) that enable increased uptake of vaccine molecules have demonstrated the highest adjuvant effects.

The toxicity of CT and LT naturally renders them unsuitable for human use. The danger of attenuated strains of viruses and bacteria to become virulent, integration of their genome into the human genome, which may activate oncogenes to cause cancer, and neutralization of these microorganisms through pre-existing immunity before they can even deliver antigens are some of the major challenges of using microorganisms for oral vaccination. Additionally, protein antigen stability can be adversely affected by organic solvents used in synthesis of polymeric micro and nanoparticles. Liposomes often have poor adjuvant effect via the oral route, and typically, inconsistent bath-to-batch quality is a problem with liposomes and ISCOMS.

Pollens/spores are hollow shells that contain plant reproductive material. Their outer wall is made of a very tough biopolymer called sporopollenin that protects the reproductive material from various physical, chemical and environmental assaults. Sporopollenin can also withstand the acidic environment of the stomach. Surprisingly, despite their relatively large size (~30 µm in diameter) it has been found that pollens/spores can travel as intact particles across the intestine into the blood in humans and animals. Furthermore, pollen/spore shells are naturally porous to allow exchange of gases, water and nutrients required by the plant reproductive structure residing inside. The present inventors have realized, but in no way a limitation of the present invention, that these properties of pollens/spores suggest a unique opportunity to exploit pollens/spores for oral (and via other routes and approaches) drug transport because pores in the pollen/spore shell could be used to first extract the native material from inside the pollens/spores, and then could be used to again fill the clean interior space with drug molecules, the chemically resistant shell of pollens/spores could safely transport drugs loaded in its interior across the harsh environment of the stomach, and upon reaching the intestines, the drug-filled pollens/spores could move into the human body carrying the drug with them. Pollens/spores can be readily cleaned with inexpensive chemicals, and then filled with molecules using mild vacuum that does not expose biological or chemical drugs to harsh denaturing conditions. It has been shown that proteins as large as 540 kDa, and a magnetic resonance imaging contrast agent, food oils including cod liver oil can be filled into pollens/spores. Another possibility, but also in no way a limitation of the present invention for why pollens work with the immunizations taught herein, is that pollen shells may activate and/or stimulate the epithelial cells lining the gut, and by doing so may somehow allow better uptake of antigen released in the intestine. Alternatively, pollens might just stay longer in intestine as they can perhaps stick to gut mucus, thus constantly releasing antigen in close proximity to epithelial cells. However, the exact mechanism of how pollens induce immune responses is not a limitation of the invention.

Pollens/spores are part of traditional medicine across the world including India, China, American Indians, Turkish folk medicine, and Papua New Guinea to name a few. They are used to treat a number of ailments including kidney disorders and stomach ache. From a more scientific western-research perspective two studies exist which show that feeding untreated or treated *lycopodium* spores to humans does not cause any adverse effects. First is a study done in 1974 where untreated *lycopodium* spores were fed to human subjects to study kinetics of *lycopodium* spore absorption into blood, and the second is a study where chemically-treated *lycopodium* spores were mixed with fish oil and fed to humans to help mask the foul taste of fish oil. Together, these different observations provide confidence that both native and cleaned *lycopodium* spores are safe for human oral consumption.

A study done in humans in 1974 demonstrated that after oral ingestion of *lycopodium clavatum* spores, 6,000 to 10,000 spores per human volunteer were absorbed into the blood stream where they could be detected by electron microscopy. This clearly shows that *lycopodium* spores can enter the human body across the intestinal mucosa as intact particles. It was further observed in the study that *lycopodium* spores in the blood defragmented (perhaps due to enzymatic action) and were cleared from the body, providing a natural mechanism of *lycopodium* spore clearance.

The present inventors have realized that in light of the prior art, including the patents listed above, it is not obvious that pollen grains can have an immune enhancing effect when included into the vaccine formulation, and one cannot predict the efficacy of pollens/spores for oral vaccination simply based on the patents and literature published before.

The scientific literature in the field of vaccines shows that there is no methodology available to predict apriori the effectiveness of a delivery system in inducing an immune response, or the effectiveness of an adjuvant-antigen combination in inducing a good immune response. For example aluminum-based adjuvants are approved by the FDA and are used in certain vaccine formulations, yet they are ineffective when used with other vaccines. To corroborate this point, we cite the following from a book on adjuvants: Cited from: Vaccine Adjuvants—Preparation Methods and Research Protocols, Edited by Derek T. O'Hagan. Humana Press; ISBN-13: 978-1617371592, Page 13 "Most adjuvants are effective with some antigens, but not others. For example, aluminum compounds failed to augment vaccines against whooping cough, typhoid fever, trachoma, adenovirus hexon antigens, influenza hemagglutinin, and *Haemophilis influenzae* type b capsular polysaccharide conjugated to tetanus toxoid. It is not always possible to predict compatible and incompatible adjuvant-vaccine combinations early in development, before the late stages of preclinical or early clinical development." Furthermore, U.S. Pat. No. 7,087, 236, discloses a vaccine formulation for enhanced, protective and controlled immune response and use of polymeric particles (in particular polylactic and polyglycolic acid copolymers) for inducing a Th1-type of immune response to *B pertussis* and disclose the use of polylactic and polyglycolic acid copolymer particles for vaccine delivery and for inducing an adjuvant effect. Despite prior art, and despite the inventors of patent U.S. Pat. No. 7,087,236 using prior art to make the polymeric microparticles, they have successfully argued that their formulation is unique because the prior art is incapable of predicting the results they have obtained. U.S. Pat. No. 7,087,236 patent explicitly states in column 2, line 40-43 that " . . . no general method for predicting or anticipating the nature of the immune response induced by an antigen in combination with a given adjuvant" and in column 3 line 4-7 the "Despite the abovementioned prior art, the ability to predict and control the type of immune response produced by a given vaccine formulation remains a goal central to immunology research."

There is nothing in the art related to pollens/spores that mentions, suggests or implies any immunological potential of pollen/spores. These patents/publications only teach that therapeutic agents, food additives and nutraceuticals can be delivered using pollens/spores. There is nothing in the art that provides that pollens/spores may have potential for vaccination and that pollens/spores may boost immune response to vaccines/antigens.

Thus, the previous patents and publications on pollens/spores do not teach that pollens/spores have potential to be used in vaccine formulations to cause increased immunogenic effects. It is certainly not obvious from these patents/publications that pollens/spores can be superior to cholera toxin in stimulating an immune response towards vaccines/antigens. The potential of pollens/spores to be included in vaccine formulations to enhance immune response could not have been predicted or foreseen from the references in the art.

EXAMPLE 1

In vivo studies in mice show that pollens/spores (specifically *lycopodium* spores) produce a strong immune response against ovalbumin as a model antigen. Ovalbumin was selected because it is a well characterized model protein that is often used to characterize new vaccination systems. Importantly, the immune response generated by pollens/spores is superior to that generated by use of cholera toxin as an oral adjuvant. Cholera toxin is widely used as a positive comparative standard to assess the efficacy of various vaccination systems/adjuvants. Pollens/spores were cleaned using a chemical cleaning procedure involving treatment with acetone, potassium hydroxide and phosphoric acid using known procedures. Briefly, 50 g of dry *lycopodium* spores were stirred in 300 mL of acetone under reflux for 4 hours. Following filtration and overnight drying, they were stirred under reflux in 450 mL of 2M potassium hydroxide for 12 hours at 90° C. (renewed after 6 hours). They were then filtered and washed with hot water (5×300 mL) and hot ethanol (5×300 mL). After drying overnight, spores were stirred under reflux for 7 days in 450 mL of orthophosphoric acid at 142° C. *Lycopodium* spores were filtered and washed sequentially with water (5×300 mL), acetone (300 mL), 2M HCl (300 mL), 2M NaOH (300 mL), water (5×300 mL), acetone (300 mL) and ethanol (300 mL). Finally, they were dried at 60° C. until constant weight was achieved. After this chemical treatment procedure, proteins, carbohydrates and lipids from the pollens/spores are removed and the pollens/spores possess an empty central capsule. This removal of plant-based biomolecules will ensure that pollens/spores will not cause allergies, and the empty space can be filled with vaccines.

TABLE 1

| Sample No. | Percent nitrogen | Percent Protein (Percent Nitrogen × 6.25) |
|---|---|---|
| 1 | 0.09 | 0.5625 |
| 2 | 0.08 | 0.5 |

As shown in Table 1, the treatment was found to be very effective and the final protein concentration in the pollen was approximately 0.5% (measured using N elemental analysis and a well-established protein factor of 6.25 to convert amount of nitrogen to protein, PerkinElmer 2400 Series II CHNS/O Analyzer).

Figure 2A:
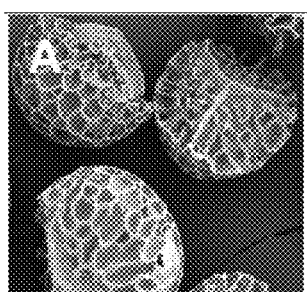
FIGS. 2A-2C are scanning electron micrographs (SEMs) of *lycopodium* spores.
Figure 2B:
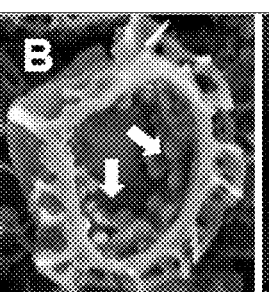
Figure 2C:
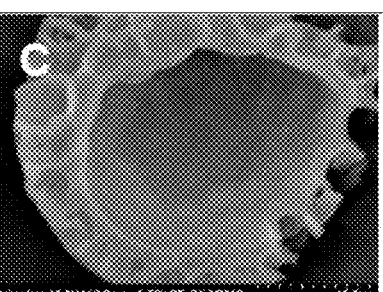

FIG. 2A shows scanning electron micrographs of *lycopodium clavatum* spores before treatment. *Lycopodium* spores before and after treatment were manually cracked to image their interior. FIG. 2B shows the biomaterial present in the *lycopodium* spores before treatment, while FIG. 2C shows that the chemical treatment successfully removed the biological material from inside the *lycopodium* spores. To fill clean and dry *lycopodium* spores with molecules, they were added to an aqueous solution containing the molecule of interest and placed in a vacuum chamber. Vacuum (~25 inch of Hg) was applied for overnight. This caused air inside the *lycopodium* spores to be removed and be replaced with the outside solution. The inward movement of the solution into the *lycopodium* spores also results in transport of the dissolved molecules into the *lycopodium* spore interior. The *lycopodium* spores were next imaged using a confocal microscope. A small amount of PGs were placed on glass cover slips and imaged with appropriate excitation/emission wavelengths. The molecules we tested were either naturally fluorescent or were chemically conjugated with a fluorescent molecule to easily visualize the molecules inside the *lycopodium* spores. Using this procedure we have evaluated a broad range of molecular size that can be introduced into the *lycopodium* spores.

Figure 2D:
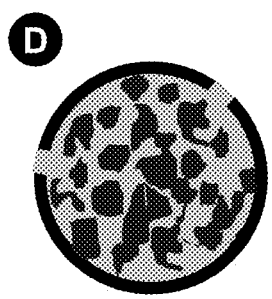
FIGS. 2D-2F are images of a schematic of the formation of a vaccine particle.
Figure 2E:
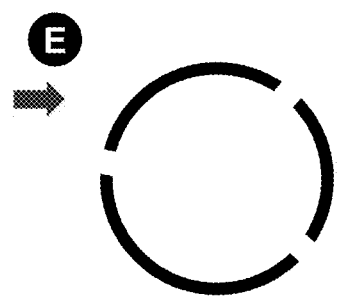
Figure 2F:
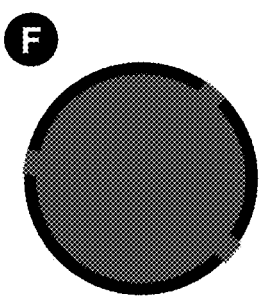
Figure 2G:
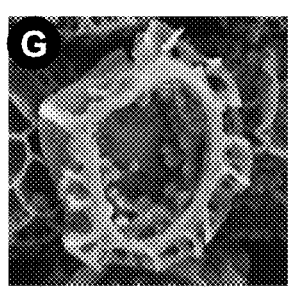
FIGS. 2G-2I are images of the formation of a vaccine particle.
Figure 2H:
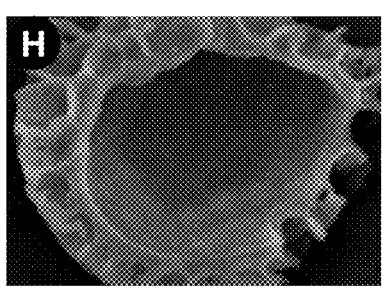
Figure 2I:
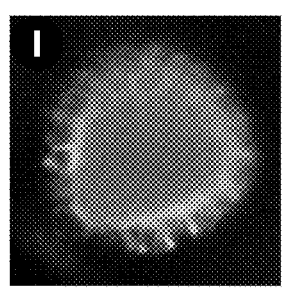

FIGS. 2D-2F are images of a schematic of the formation of a vaccine particle. As seen in FIG. 2D a spore is depicted with the contents inside the inner cavity and FIG. 2G is an image of the same. In FIG. 2E a spore is depicted with the contents removed from the inner cavity and FIG. 2H is an image of the same. In FIG. 2F a spore is depicted with the contents replaced inside the inner cavity and FIG. 2I is an image of the same.

Figure 6:
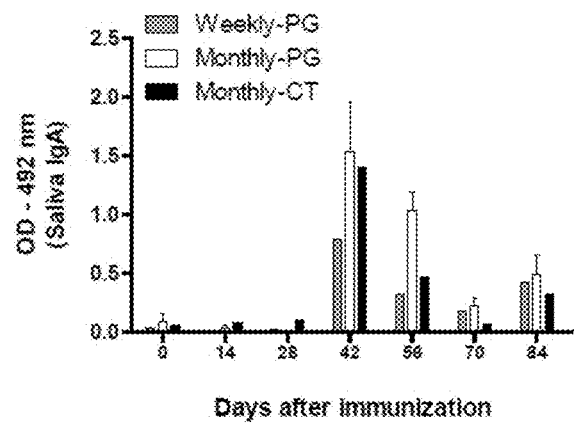
Figure 7:
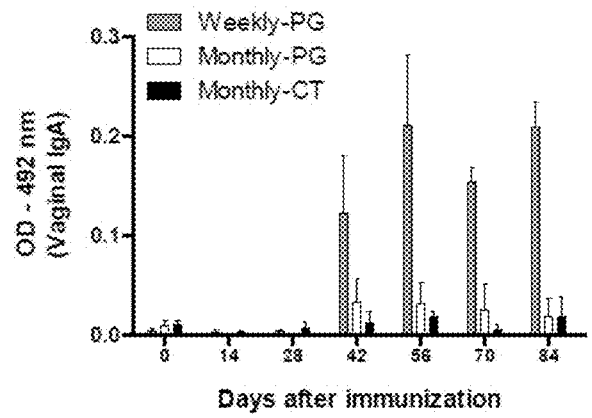

FIGS. 3A-3G are confocal micrographs of filled *lycopodium* spores. FIG. 3A is an image of unfilled spores, FIG. 3B is an image of spores filled with sulforhodamine (558 Da), FIG. 3C is an image of spores filled with dextran conjugated to fluorescein isothiocyanate (4000 Da), FIG. 3D is an image of spores filled with ovalbumin conjugated to texas red (45,000 Da), FIG. 3E is an image of spores filled with bovine serum albumin conjugated to texas red (67,000 Da), FIG. 3F is an image of spores filled with recombinant protective antigen of anthrax conjugated to Alexa Fluor 555 (83,000 Da), and FIG. 3G is an image of spores filled with dextran conjugated to fluorescein isothiocyanate (2000,000 Da). FIG. 3 shows that we could see molecules with as much as 2000,000 Da molecular weight inside the *lycopodium* spores. *Lycopodium* spores are naturally fluorescent in the blue, red and green emissions. Thus, we scanned the samples with both red and green emissions to obtain dual-colored overlay images shown in FIG. 3. Fluorescence inside the *lycopodium* spores is due to the molecule filled into the *lycopodium* spores.

To test whether pollens/spores have the ability to induce immune response against vaccines, we formulated clean-and-dry *lycopodium* spores with ovalbumin (OVA). OVA is a well characterized model vaccine antigen. We used Balb/c mice for his study. Study 1 evaluates the effect of *lycopodium* spore dose on oral vaccination: *Lycopodium* spores were added to an aqueous ovalbumin solution and vacuum was applied overnight. Any decrease in volume during vacuum application was compensated by addition of fresh water. The formulation was fed to mice (0.3 ml total) using a feeding needle. The protocol was approved by IACUC at Texas Tech University. Table 2 shows the various groups of mice included in the study.

TABLE 2

| Group code | Formulation used as oral vaccine (Composition per dose) | Group objective |
|---|---|---|
| OVA | Ovalbumin (OVA) (100 μg) | Negative control |
| CT1 | OVA (100 μg) + Cholera toxin-Holotoxin (5 μg) | Positive control |
| CT2 | OVA (5 mg) + Cholera toxin-Holotoxin (5 μg) | Positive control |
| CTB | OVA (100 μg) + Cholera toxin-B subunit (50 μg) | Positive control |
| LS1 | OVA (100 μg) + *Lycopodium* spores (1 mg) | Test group |
| LS5 | OVA (100 μg) + *Lycopodium* spores (5 mg) | Test group |

Mice: n = 5 per group
Immunization dose: 2 times, one on day '0', and another on day '28'

FIGS. 4A and 4B are graphs of OVA specific IgG antibody response in mice serum. FIG. 4A is a graph of a titration curve for pooled day 56 serum. FIG. 4B is a graph of IgG antibody in 1:200 diluted serum of individual mice of a group. Each circle represents an animal in a group. The short horizontal bar represents the mean. To evaluate the potential of *lycopodium* spores for oral vaccination, we immunized Balb/c mice orally with ovalbumin (OVA) formulated with *lycopodium* spores. Based on previously published work, we selected a dose of 100 μg for OVA, while *lycopodium* spores dose was tested at two levels—1 mg and 5 mg. In addition, we used CT (5 μg) and the safer but less immunogenic B subunit of CT (CTB—50 μg) as positive control adjuvants. It has been shown that CT is more effective if a higher dose of OVA is used. Accordingly we also included a group of mice fed with 5 mg OVA and 5 μg CT. Mice were orally immunized at days 0 and 28. Blood was collected at days 0, 28 and 56 to determine anti-OVA immunoglobulin G (IgG) levels using enzyme-linked immunosorbent assay (ELISA). Starting with a 1:50 dilution of 'pooled' serum (day 56) an antibody titration curve was obtained (FIG. 4A). At each serum dilution the optical density (OD) of LS5 (i.e., OVA fed with 5 mg LS) was the highest. From this data, we next observed that the ELISA OD value at 1:200 serum dilution was in the linear range of all the groups. Accordingly, to help compare the different groups we performed an ELISA using day 0, 28 and 56 individual mouse serum at 1:200 dilution (FIG. 4B). Data in FIG. 4B shows that: (i) OVA alone does not produce a high antibody response when given orally. (ii) Use of CT as adjuvant with OVA increases the immune response compared to OVA alone (OVA vs CT1). By using CT as an adjuvant if the OVA dose is increased from 100 μg to 5 mg (i.e. CT1 vs CT2) the IgG production increases by almost four fold; and (iii) Mice immunized with 100 μg OVA+5 mg LS (LS5 group) had IgG levels even higher (about 10-fold higher) than the 5 mg OVA+5 μg CT group (CT2). This is exciting data because CT is one of the testing standards for oral mucosal vaccination and our data shows that *lycopodium* spores are even superior to CT. Overall, this study provides strong foundation to the idea that pollens/spores have adjuvant function in a vaccine formulation.

Study 2 examines the effect of frequency of vaccination using *lycopodium* spores as adjuvants to investigate the immunological effect of feeding mice with a vaccine formulation containing pollens/spores more frequently than the monthly interval, which was investigated in Study 1. Balb/c mice (n=3-5 per group) were orally immunized weekly or monthly. The various groups of this study are shown in Table 3.

TABLE 3

| Group code | Formulation given as vaccine through oral route. (Composition per dose) | Group objective | Vaccine delivered on (days) |
|---|---|---|---|
| Weekly-PG | Weekly-Ovalbumin 100 μg + lycopodium spores 2 mg | Test group | 1, 8, 15, 22, 29, 36, 43, 50, 57, 64, 71, and 78 |
| Monthly-PG | Monthly-Ovalbumin 100 μg + *lycopodium* spores 2 mg | Test group | 1, 29 and 57 |
| Monthly-CT | Monthly-Ovalbumin 100 μg + Cholera toxin (Holotoxin) 1 μg | Positive control | 1, 29 and 57 |

Blood, Saliva and Vaginal washes were collected at days 0, 14, 28, 56, 70 and 84 to determine anti-ovalbumin immunoglobulin G (IgG) levels in serum and immunoglobulin A (IgA) levels in saliva and vaginal wash using enzyme-linked immunosorbent assay (ELISA).

FIG. 5 is a graph of Anti-OVA IgG levels in serum. As shown in FIG. 5, a monthly dose of 2 mg *lycopodium* spores formulated with ovalbumin produces a higher level of IgGs in the serum compared to use of cholera toxin as adjuvant. Furthermore, upon increasing the dosage frequency from monthly to weekly, for the 2 mg *lycopodium* spore formulation with ovalbumin as antigen, an even higher immune response was generated resulting in high IgG levels in the serum.

FIG. 6 is a graph of Anti-OVA IgA levels in saliva. FIG. 7 is a graph of Anti-OVA IgA levels in vaginal wash. Upon comparing the mucosal immune responses we found that IgA antibodies were induced both in saliva (FIG. 6) and vaginal washes (FIG. 7). The IgA levels were higher or equal for the 2 mg *lycopodium* spores+ovalbumin group (both monthly and weekly frequency groups) than the cholera toxin group. This experiment overall shows the ability of *lycopodium* spores to induce not just systemic immune responses but also mucosal immune responses. It also shows that frequency of dose administration can further be used as a method to control immune response with pollens/spores.

Study 3 provides methods that can enhance retention of vaccine/antigens inside pollens/spores. The mechanism of how pollens/spores potentiate a strong immune response is not clear. Possible mechanisms might be that pollens/spores carry the vaccines/antigens inside their 'belly/interior' into the body, or the vaccine/antigen molecules adsorb/attach onto pollen/spore walls and are carried into the body, or vaccine/antigen molecules adsorb/attach into pores in pollen/spore wall and are carried into the body, where they interact with the immune system. Because vaccines/antigens are quite readily introduced into the pollen/spore 'belly', it is then also quite possible that the vaccine/antigen molecules start to diffuse out when the formulation is fed to animals due to dilution in the stomach fluids. Therefore, it might be of benefit to slow down the rate at which vaccines/antigens start to come out of the pollens/spores, which might then further increase the amount of vaccine/antigen being carried by the pollens/spores into the body. This might further help increase the immune response.

To achieve the effect of increasing residence time of antigens/vaccines inside pollens/spores we have attempted the following: Synthesis of gold nanoparticles as antigen/vaccine anchoring points inside PGs. It is known that various biomolecules including proteins and DNA can adsorb onto the surface of gold nanoparticles. This phenomenon is well known and is actively used to conjugate various biomolecules to the gold nanoparticles. We hypothesized that by synthesizing gold nanoparticles inside pollens/spores we could provide a surface for the antigen/vaccine molecules to attach/adsorb to. If the gold nanoparticles are large enough they can stay entrapped inside the pollens and thereby they can also help retain antigens attached to their surface inside the pollens/spores. We have successfully prepared gold nanoparticles inside *lycopodium* spores by the Turkevich method with modification. Briefly, we first mixed *lycopodium* spores with a solution containing hydrogen tetrachloroaurate and sodium citrate. Vacuum was applied and the resulting suspension was centrifuged and washed once in water. The resulting suspension was then heated to initiate the reduction of hydrogen tetrachloroaurate to gold nanoparticles. To verify the formation of gold nanoparticles inside *lycopodium* spores we sectioned the *lycopodium* spores and visualized them under a transmission electron microscope (TEM).

Figures 8A, 8B:
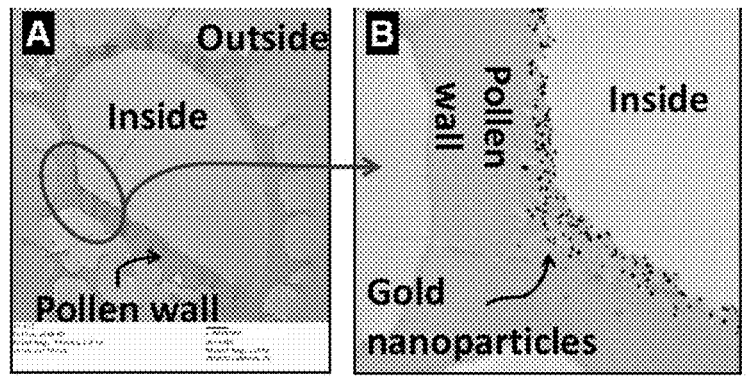

FIGS. 8A and 8B are transmission electron micrographs of *lycopodium* spores with gold nanoparticles. FIG. 8A is a TEM image of the Section of a single spore, FIG. 8B is a TEM image of the Zoom-in of a portion of the spore. From FIGS. 8A-8B it can be seen that gold nanoparticles were successfully formed inside the *lycopodium* spores.

To achieve the effect of increasing residence time of antigens/vaccines inside pollens/spores, we have also attempted the synthesis of hydrogels inside pollens/spores: Hydrogels are materials that can absorb water and swell. We postulated that if hydrogels can be synthesized inside pollens/spores they could entrap water along with the antigen/vaccine, and thus slow the diffusive outward movement of the entrapped molecules. Much like the spaghetti/noodles can hinder movement of particles, the hydrogel molecules will similarly create a network of large polymeric molecules that will absorb water+vaccine/antigen and also make it difficult for the molecules to diffuse out. Furthermore, if the hydrogels are for example temperature or pH sensitive such that they shrink when introduced in the stomach, they could further increase the entrapment and increase the resistance to outward diffusion of antigens due to tighter spacing between polymeric molecules in shrunk state. We have prepared poly(N-isoproylacrylamide) (pNIPAm), a temperature sensitive hydrogel inside the *lycopodium* spores using the following methodology. Purified water (MilliQ) was used throughout. N-Isopropylacrylamide (NIPAm) (Acros Organic LOT:A0281390), ammonium persulfate (APS) (Fisher Scientific LOT:103649) and N,N,N',N'-tetramethyl ethylenediamine (TEMED) (Acros Organic LOT: A0285456) were used as purchased. p-NIPAm polymer was synthesized inside treated pollen using the APS initiator and TEMED catalyst redox mechanism. NIPAm solution (250 ml, 2M) was nitrogen purged for 30 minutes and stored in a sealed container. Pollens (3 g) and NIPAm solution (35 ml) were mixed and vacuumed (−25 in.Hg) for one hour to fill the pollen interior with NIPAm, centrifuged at 4400 rpm for 30 minutes and the supernatant was removed in order to avoid excessive polymer gelation outside of pollens. Polymerization was initiated by addition of APS solution (1 wt % 0.5 ml). The mixture was quickly stored in 4° C. environment after the addition of TEMED (1 wt % 0.5 ml) and allowed to polymerize for 12 hours. The resulting polymer gel was washed with water and centrifuged (4400 rpm) at least 20 times until excessive polymer on the pollen surface was removed. The pollens were then oven dried at 50° C. until constant weight was reached and sent for TEM imaging.

Figure 9:
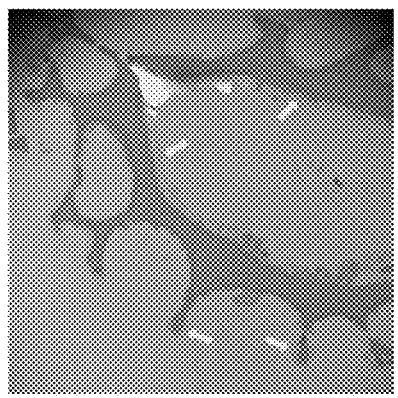

FIG. 9 is a transmission electron micrograph of a sectioned *lycopodium* spore. A thin film of polymer can be seen inside the pollen and on the outer surface of the *lycopodium* spore. This demonstrates that we can synthesize pNIPAm inside the *lycopodium* spores for potential use to enhance retention of vaccines/antigens inside *lycopodium* spores. The above two methodologies also potentially limit degradation of antigens/vaccines by the degradative enzymes of the stomach. This can be achieved because most of the vaccines/antigens will remain localized inside the pollen/spore 'belly', and the enzymes will have to enter the pollen/spores to cause degradation. While enzymes could enter the pollens/spores, their numbers would be limited and hydrogels will further provide a barrier to their entry and to freely access the vaccine/antigen molecules. Gold nanoparticles will likewise provide protection to degradation by enzymes by hindering free access of vaccine/antigen molecules by the enzymes because vaccines/antigens will be attached/adsorbed to gold nanoparticles. Similarly other anchoring methodologies either via chemical bonds or other physical approaches could be used to retain vaccines/antigens inside pollens/spores, or on the surface of pollens/spores, or inside pores of the pollens/spores.

Study 4 shows methodology to further enhance the adjuvant effect of PGs. Clearly various known adjuvants such as CpG rich oligonucleotides, flagellin, imiquimod, gardiquimod, monophosphoryl lipid-A, polyriboinosinic polyribocytidylic acid [poly(I:C)] and other molecules can be added to the vaccine formulation containing pollens/spores to help increase the immune response even further. This methodology is quite intuitive. However, the approach not so intuitive as to synthesize aluminum-based FDA-approved particles as adjuvants inside the spores/pollens. One instance of making alum-based adjuvants inside pollens/spores can be to simply take a soluble form of aluminum such as aluminum chloride, fill it inside the pollens/spores, and react the resulting suspension of pollens/spores with a base such as sodium hydroxide. This will cause precipitation of aluminum hydroxide inside the pollens/spores, and vaccines/antigens can then be added to attach/adsorb them onto aluminum hydroxide. We have tested this approach by making aluminum hydroxide particles inside pollens. Likewise, we have also synthesized iron oxide particles inside pollens. Briefly, an aqueous solution of ferrous chloride and ferric chloride was made to which dry and clean *lycopodium* spores were added. Vacuum was subsequently applied to fill ferrous and ferric chloride into the *lycopodium* spore interior. After a quick wash, the spores/pollens were added to an ammonium hydroxide solution, which caused reduction of ferric and ferrous ions to iron nanoparticles. The pollens/spores were thoroughly washed to remove any particles formed on the outer surface of pollens/spores.

Figure 10A:
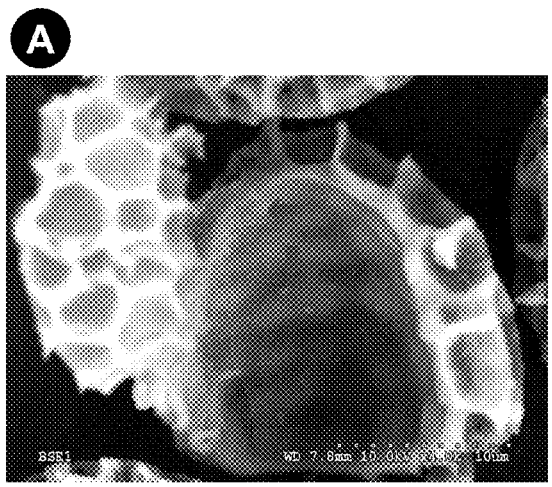
Figure 10B:
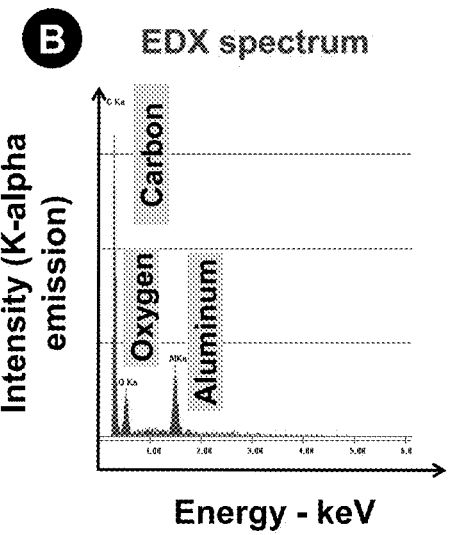
Figure 10C:
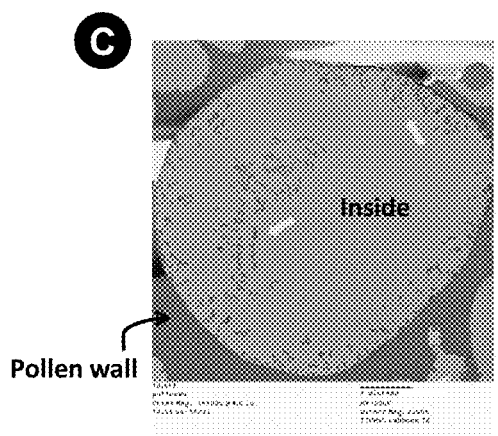

FIG. 10A is a scanning electron micrograph of a *lycopodium* spore cracked manually to help visualize aluminum hydroxide particles inside the spores. The arrows point to the light colored aluminum hydroxide particles. FIG. 10B is an electron dispersive x-ray analysis of these particles to confirm that they are indeed aluminum particles. The peak for aluminum in the EDX spectrum confirms that the particles are composed of aluminum. FIG. 10C is a transmission electron micrograph of a *lycopodium* spore. The black spots/specks are the iron oxide particles.

Figure 11:
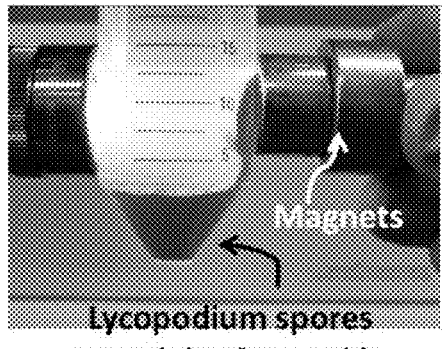

FIG. 11 is a photograph of *lycopodium* spores containing iron oxide microparticles being magnetically held on the side of a plastic tube. All of the studies above were done using spores of *lycopodium clavatum* as a representative example of pollens/spores, but this does not restrict our claim to this species.

The pollen/spore may for example further be spiny-surfaced pollen grains of paper mulberry (*Broussonetia papyrifera*); corn (*Zea mays*); Cocklebur (*Xanthium commune*); Goldenrod (*Solidago* spp.); Poverty weed (*Iva axillaris*); Desert Ragweed (*Ambrosia dumos*); False Ragweed (*Ambrosia acanthicarpa*); Giant Ragweed (*Ambrosia trifida*); Short Ragweed (*Ambrosia artemisifolia*); Slender Ragweed (*Ambrosia tenuifolia*); Southern Ragweed (*Ambrosia bidentata*); Western Ragweed (*Ambrosia psilostachya*); Prairie Sage (*Artemisia ludoviciana*); Common Sagebrush (*Artemisia tridentate*); Annual Wormwood (*artemisia annua*); Marsh Elder; and High-Water Shrub.

EXAMPLE 2

Evaluate the effect of neutralization of gastric acid on the immune response produced using *lycopodium* spores. Rationale: Various oral vaccination studies (see references 1-8 below) have in the past neutralized the gastric acid to help improve vaccine efficacy. The inventors investigated how neutralization of stomach acid affects the immune response elicited using the oral vaccine formulation based on *lycopodium* spores (as a representative of pollen grains in general).

Methods and results: To examine the effect of neutralization of gastric acid, animals were deprived of food and water 2 hours prior to the immunizations. Then they were given an oral gavage of 0.3 ml of sodium bicarbonate (8 parts phosphate buffered saline (PBS)+2 parts 0.34M sodium bicarbonate) (references 1-4 below). Table 4 shows the various groups of mice included in the study. The animals were orally immunized with 0.3 ml of the vaccine formulation 30 minutes after the sodium bicarbonate treatment. The control groups were fed with 0.3 ml of the vaccine formulation without pre-feeding them sodium bicarbonate. The animals were immunized on day 0 and 28 while serum samples were collected on days 0, 28 and 56. The samples were processed and serum was stored at −20° C. until analyzed. The protocol was approved by IACUC at TTU. While the data was generated using *lycopodium* spores (LSs), the present invention can be used to prepare oral vaccines with all pollen grains.

TABLE 4

| Group code | Formulation used as oral vaccine (Composition per dose) |
|---|---|
| OVA | Ovalbumin (OVA) (100 µg) |
| OVA-Na | Prefeed Sodium bicarbonate + OVA (100 µg) |
| LS5 | OVA (100 µg) + *Lycopodium* spores (5 mg) |
| LS5-Na | Prefeed Sodium bicarbonate + OVA (100 µg) + *Lycopodium* spores (5 mg) |

Mice: n = 5 per group
Immunization dose: 2 times, one on day '0', and another on day '28'

Figure 12A:
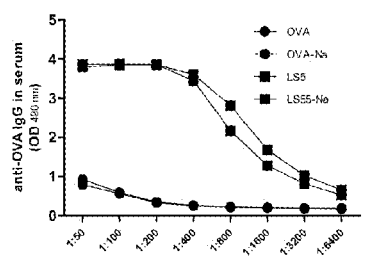
Figure 12B:
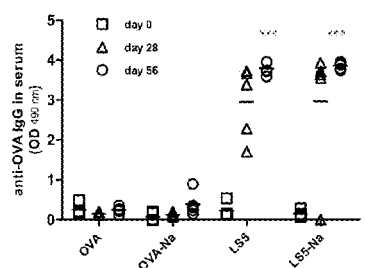

Serum was analyzed to determine anti-OVA immunoglobulin G (IgG) levels using enzyme-linked immunosorbent assay (ELISA). Starting with a 1:50 dilution of 'pooled' serum from each group at day 56, an antibody titration curve was obtained (FIG. 12A). At each serum dilution the optical density (OD) of LS5 and the LS5-Na groups were not significantly different. Next, to help compare the different groups the inventors performed an ELISA using day 0, 28 and 56 individual mouse serum at 1:400 dilutions (FIG. 12B). The results obtained were analyzed using the two-way ANOVA test with Bonferroni test for statistical analysis. The day 56 response of LS5 and LS5-Na groups were found to be significantly ($p<0.001$) higher when compared to OVA and OVA-Na. Data in FIG. 12B shows that: (i) OVA alone does not produce a high antibody response when given orally. Even neutralization of gastric acid before immunization does not enhance the response significantly; (ii) Both the *lycopodium* spore groups (LS5 and LS5-Na) show high anti-OVA IgG levels and (iii) The IgG levels with (LS5-Na group) and without (LS5 group) prior neutralization of gastric acid are not significantly different.

Figure 12C:
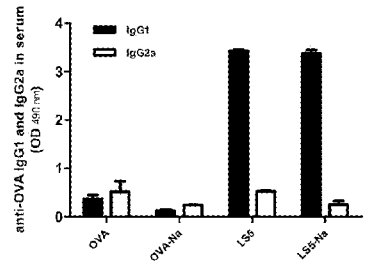

The pooled serum samples were also analyzed for IgG subtypes at the same dilution (FIG. 12C). FIG. 12C shows that LS-based vaccination elicits a higher IgG1 response compared to IgG2a, and this trend is not affected by the use of sodium bicarbonate to neutralize gastric acid.

This data shows that *lycopodium* spores are capable of producing an immune response after oral immunization that is unaffected by the gastric acidity in the case of ovalbumin as antigen.

To evaluate the effect of neutralization of gastric acid on the immune response produced against anthrax antigen using *lycopodium* spore-based oral vaccination. The inventors next assessed whether pollen grain-based oral vaccination can help induce an immune response towards other vaccine antigens apart from ovalbumin and if gastric neutralization has a role to play.

Methods and results: Anthrax recombinant protective antigen (rPA) was selected as the vaccine antigen to assess whether pollen grain-based oral vaccination can help induce an immune response towards rPA. rPA is known to be unstable at extreme temperatures and pH values (reference 9 below). Therefore, we decided to evaluate the response from rPA-*lycopodium* spore formulation both with and without neutralization of stomach acid. Table 5 shows the various groups of mice included in the study. To examine the effect of neutralization of gastric acid animals were deprived of food and water 2 hours prior to the immunizations. Then they were given an oral gavage of 0.3 ml of sodium bicarbonate (8 parts PBS+2 parts 0.34M sodium bicarbonate). The animals were orally immunized with 0.3 ml of the vaccine formulation 30 minutes after the sodium bicarbonate treatment. The control groups were fed with 0.3 ml of the vaccine formulation without pre-feeding them sodium bicarbonate. The animals were immunized on days 0, 21 and 42 while serum samples were collected on days 0, 21, 42 and 63. The samples were processed and serum was stored at −20° C. until analyzed. The protocol was approved by IACUC at TTU.

TABLE 5

| Group code | Formulation used as oral vaccine (Composition per dose) |
|---|---|
| rPA | Anthrax recombinant protective antigen (rPA) (100 µg) |
| rPA-Na | Prefeed Sodium bicarbonate + rPA (100 µg) |
| rPA + LS5 | rPA(100 µg) + *Lycopodium* spores (5 mg) |
| rPA + LS5-Na | Prefeed Sodium bicarbonate + rPA(100 µg) + *Lycopodium* spores (5 mg) |

Mice: n = 5 per group
Immunization dose: 3 times, on days '0', 21 and '42'

Figure 13A:
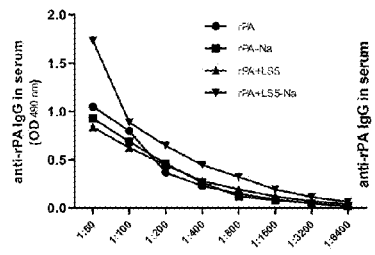
Figure 13B:
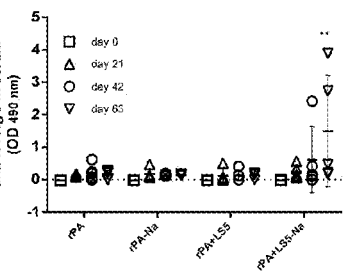

Serum was analyzed to determine anti-rPA immunoglobulin G (IgG) levels using enzyme-linked immunosorbent assay (ELISA). Starting with a 1:50 dilution of 'pooled' serum (day 63) an antibody titration curve was obtained (FIG. 13A). At each serum dilution the optical density (OD) of LS5 and the LS5-Na groups were not significantly different. To help compare the different groups we performed an ELISA using day 0, 21, 42 and 63 individual mouse serum at 1:100 dilution (FIG. 13B). The results obtained were analyzed using the two-way ANOVA test followed by the Bonferroni test. Data in FIG. 13B shows that: (i) rPA alone does not produce a high antibody response when given orally. Even neutralization of gastric acid before immunization does not enhance the response significantly; (ii) Amongst the *lycopodium* spore groups (rPA+L55-Na) shows higher anti-rPA IgG levels; and (iii) The IgG levels with (rPA+LS5-Na group) and without (rPA+LS5 group) prior neutralization of gastric acid are significantly different.

Figure 13C:
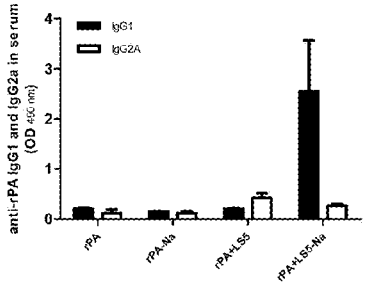
Figure 14:
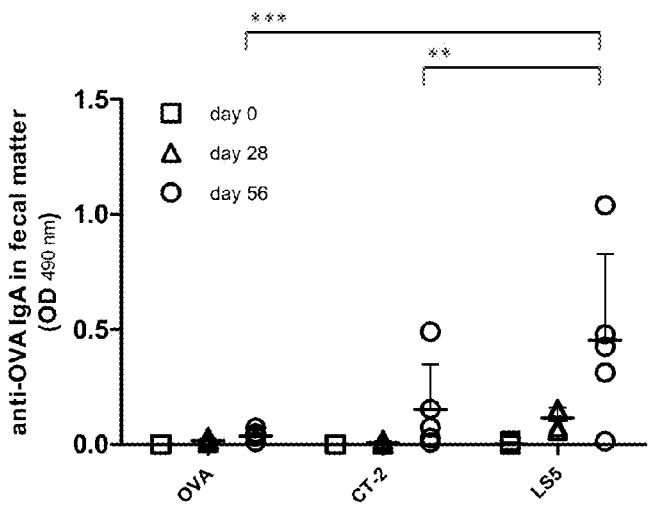

The pooled serum samples were also analyzed for IgG subtypes at the same dilution (FIG. 13C). FIG. 13C shows that LS-based vaccination elicits a higher IgG1 response compared to IgG2a with the rPA+LS5-Na group.

This data is important because it shows that *lycopodium* spores are capable of producing an immune response after oral immunization towards rPA, an anthrax antigen. Coupled with immune response towards ovalbumin, this demonstrates a more universal applicability of pollens for oral vaccination against different antigens.

Figure 15A:
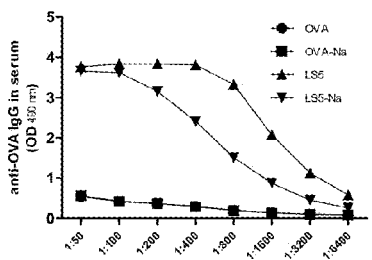
Figure 15B:
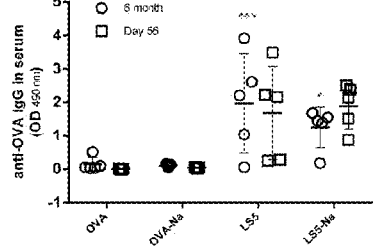
Figure 15C:
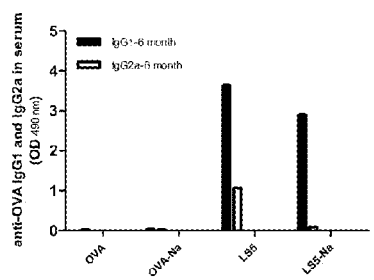

Determine the ability of *lycopodium* spores to produce a mucosal immune response at gastrointestinal mucosa. Since pollen grain-based vaccination is performed orally, the inventors determined whether secretory immunoglobulin A (IgA) specific to the antigen can be stimulated at the gastrointestinal mucosa.

Methods and results: To determine the mucosal immune response produced the animals were given an oral gavage of formulation as described in Table 6. The animals were immunized on days 0 and 28 while fecal droppings were collected on days 0, 28 and 56. The samples were processed in buffer to get extracts, clarified by centrifugation, and stored at −20° C. until analysis. The protocol was approved by IACUC at TTU.

TABLE 6

| Group code | Formulation used as oral vaccine (Composition per dose) |
|---|---|
| OVA | Ovalbumin (OVA) (100 μg) |
| CT2 | OVA (5 mg) + CT (5 μg) |
| LS5 | OVA (100 μg) + *Lycopodium* spores (5 mg) |

Mice: n = 5 per group
Immunization dose: 2 times, one on day '0', and another on day '28'

Fecal extracts were analyzed to determine anti-OVA immunoglobulin A (IgA) levels using enzyme-linked immunosorbent assay (ELISA). 1:5 dilution was chosen for analyzing the individual animal samples. The results obtained were analyzed using the two-way ANOVA test followed by the Bonferroni test. Data in FIG. 14 shows that: (i) OVA alone does not produce a high mucosal IgA antibody response when given orally; (ii) the *lycopodium* spore group (LS5) shows measurable IgA levels; and (iii) the IgA levels of the LS5 are higher than that of the CT2 group. CT is one of the testing standards for oral mucosal vaccination and these data shows that *lycopodium* spores are superior to CT in producing a mucosal immune response.

Evaluate the ability of *lycopodium* spores to induce a long-term immune response. Next, the inventors assessed whether the antigen specific immune response produced from pollens is short lived or if it persists longer. A long-persisting immune response is desirable to help maintain long-term vaccine protection.

Methods and results: To study the ability of *lycopodium* spores to produce an immune response that persists over a long period of time the following study was performed. Animals were deprived of food and water 2 hours prior to the immunizations. Then they were given an oral gavage of 0.3 ml of sodium bicarbonate (8 parts PBS+2 parts 0.34M sodium bicarbonate). The animals were orally immunized with 0.3 ml of the vaccine formulation 30 minutes after the sodium bicarbonate treatment. Table 7 shows the various groups of mice included in the study. The animals were immunized on day 0 and 28 while serum samples were collected 1 month (called day 56) and 6 months after the second immunization. The animals were not given any other dose of the vaccine during this period. The samples were processed to get serum and stored at −20° C. until analysis. The protocol was approved by IACUC at TTU.

TABLE 7

| Group code | Formulation used as oral vaccine (Composition per dose) |
|---|---|
| OVA | Ovalbumin (OVA) (100 μg) |
| OVA-Na | Prefeed Sodium bicarbonate + OVA (100 μg) |
| LS5 | OVA (100 μg) + *Lycopodium* spores (5 mg) |
| LS5-Na | Prefeed Sodium bicarbonate + OVA (100 μg) + *Lycopodium* spores (5 mg) |

Mice: n = 5 per group
Immunization dose: 2 times, one on day '0', and another on day '28'

Serum was analyzed to determine anti-OVA immunoglobulin G (IgG) levels using enzyme-linked immunosorbent assay (ELISA). Starting with a 1:50 dilution of 'pooled' serum an antibody titration curve was obtained (FIG. 15A). At each serum dilution the optical density (OD) of LS5 and the LS5-Na groups were not significantly different. To help compare the different groups we performed an ELISA using day 56 and 6 month individual mouse serum at 1:400 dilution (FIG. 15B). The results obtained were analyzed using the two-way ANOVA test followed by the Bonferroni test. Data in FIGS. 15B and 15C shows that: (i) OVA alone does not show a high antibody response when given orally. Even neutralization of gastric acid before immunization does not enhance the immune response significantly; (ii) both the *lycopodium* spore groups (LS5 and LS5-Na) show high IgG levels even after 6 months. These antibody levels are comparable to that observed 56 days after the first immunization; and (iii) as with day 56 (FIG. 1C), IgG1 subtype is higher compared to IgG2a subtype even at 6 months.

Again, the present inventors demonstrate for the first time that *lycopodium* spores are capable of producing an immune response that persists for a long time after immunization. Overall, this is significant as it shows that a vaccine formulated using pollens/spores produces an immune response that persists for a long term without further exposure to the vaccine. This may eliminate the need to administer multiple doses of the vaccine to maintain the immune response.

Evaluate the ability of *lycopodium* spores to induce memory natural killer cells. Natural killer (NK) cells are very potent at killing infected cells. Recently it has been found that NK cells, which are traditionally considered part of the innate immune system, can actually be antigen-specific and can have memory, properties that are part of the adaptive immune system. Thus we sought to determine if *lycopodium* spores can induce antigen specific memory NK cells. Induction of antigen-specific memory NK cells could be of immense value as NK cells can use even non-neutralizing antibodies to kill cells. This is of value in the context of diseases like HIV, against which it has been tough to develop vaccine-induced broadly-reactive neutralizing antibodies to HIV. Instead, if anti-HIV NK cells could be induced via vaccination, it might be possible to kill the first cell being infected in the host, thus clearing HIV before it can gain foot-hold. In general the NK cells could be effective against different infectious agents, and even cancer.

Figure 16A:
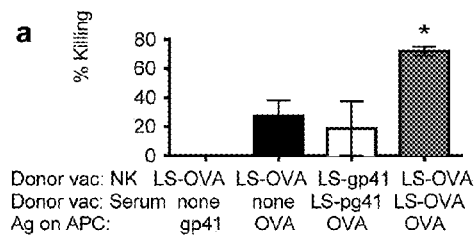
Figure 16B:
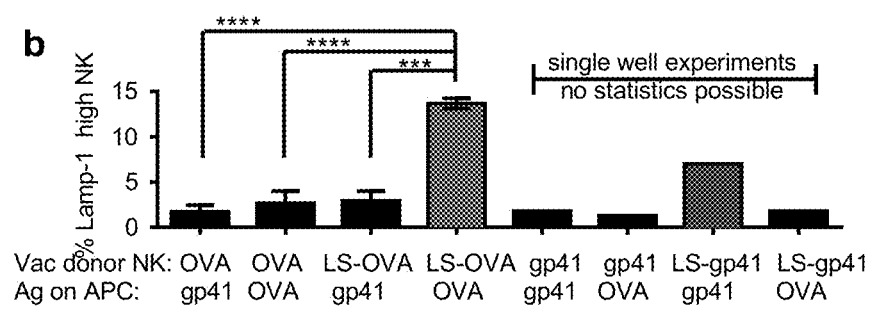

Methods and results: In this study, two antigens, ovalbumin and HIV gp41 were used as antigens. To test whether *lycopodium* spore-based oral vaccination results in the induction of NK cell memory, whether NK cells can be recruited to the GI mucosa and/or draining LNs, and whether NK cells in vaccinated animals are capable of Ag-specific Lamp-1-upregulation, killing and antibody-dependent cell-mediated cytotoxicity (ADCC), we compared NK cell functions and locations in OVA (100 µg) to LS(5 mg)-OVA(100 µg) (LS-OVA) vaccinated mice after oral challenge. In mice vaccinated with LS-OVA vaccine, oral challenge with LS-OVA resulted in a 10-fold increase in the numbers of NK cells in the mesenteric lymph nodes (MLNs) compared to OVA vaccinated controls. Further, LS-OVA primed NK cells killed OVA loaded target cells, but not gp41 loaded targets, and addition of serum from LS-OVA vaccinated mice significantly increased killing in an Ag-specific manner, while serum from LS-gp41 mice failed to elicit ADCC (FIG. 16A). Importantly, NK cells only degranulated to OVA-loaded APC, as shown by Lamp-1 upregulation, but failed to degranulate to a new antigen (FIG. 16B). The inventors also tested whether LS-gp41 vaccination induced memory NK cells in mice. Indeed, NK cells from LS-gp41 vaccinated mice upregulated Lamp-1 when stimulated with gp41 loaded APC, but not in response to OVA loaded APC. As with OVA, successful oral vaccination required the use of pollen-grain as a vehicle, as oral vaccination with gp41 alone did not elicit NK cell memory (FIG. 16B). This data shows that vaccination of mice with LS-OVA or LS-gp41 elicits strong NK cell mediated adaptive immune responses having antigen specificity and memory, including ADCC.

The composition may be for suitable and/or adapted and/or intended for oral delivery of an active substance to a surface, in which case the surface may be a living surface (again, either plant or animal) or an inanimate surface. The ability of the pollen/spore to act as a physical barrier protecting an encapsulated active substance, can be of particular significance in this context, since on release of the active substance onto a surface, the substance will then be exposed on the outside of the pollen/spore.

The present invention provides a composition for "oral" administration that may be suitable and/or adapted and/or intended for oral application. A living surface may be either plant or animal, in particular animal, and in the case of an animal surface may either be human or non-human, in particular human.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s)

or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Vajdy, M. and N. Y. Lycke (1992). "Cholera toxin adjuvant promotes long-term immunological memory in the gut mucosa to unrelated immunogens after oral immunization." Immunology 75(3): 488-492.

2. Snider, D. P., J. S. Marshall, et al. (1994). "Production of IgE antibody and allergic sensitization of intestinal and peripheral tissues after oral immunization with protein Ag and cholera toxin." J Immunol 153(2): 647-657.

3. Marinaro, M., H. F. Staats, et al. (1995). "Mucosal adjuvant effect of cholera toxin in mice results from induction of T helper 2 (Th2) cells and IL-4." J Immunol 155(10): 4621-4629.

4. Xu-Amano, J., H. Kiyono, et al. (1993). "Helper T cell subsets for immunoglobulin A responses: oral immunization with tetanus toxoid and cholera toxin as adjuvant selectively induces Th2 cells in mucosa associated tissues." J Exp Med 178(4): 1309-1320.

5. Summerton, N. A., R. W. Welch, et al. (2010). "Toward the development of a stable, freeze-dried formulation of Helicobacter pylori killed whole cell vaccine adjuvanted with a novel mutant of Escherichia coli heat-labile toxin." Vaccine 28(5): 1404-1411.

6. Kirkpatrick, B. D., K. M. Tenney, et al. (2005). "The novel oral typhoid vaccine M001ZH09 is well tolerated and highly immunogenic in 2 vaccine presentations." J Infect Dis 192(3): 360-366.

7. Tacket, C. O., M. B. Sztein, et al. (2000). "Phase 2 clinical trial of attenuated Salmonella enterica serovar typhi oral live vector vaccine CVD 908-htrA in U.S. volunteers." Infect Immun 68(3): 1196-1201.

8. Bishop, A. L. and A. Camilli (2011). "Vibrio cholerae: lessons for mucosal vaccine design." Expert Rev Vaccines 10(1): 79-94.

9. Jiang, G., S. B. Joshi, et al. (2006). "Anthrax vaccine powder formulations for nasal mucosal delivery." Journal of Pharmaceutical Sciences 95(1): 80-96.

What is claimed is:

1. A method of modulating an immune response in a subject comprising the steps of:
   identifying that the subject is in need of immunostimulation;
   providing an immunogenic composition comprising an intact plant spore disposed in a pharmaceutical carrier for delivery to a subject, wherein the plant spore comprises multiple pores, wherein the pores comprise one or more protein antigens disposed in an interior of the plant spore and a cryoprotectant; and
   administering the immunogenic composition to the subject to cause an immune response to the antigen.

2. The method of claim 1, wherein the modulation comprises an increase in the immune response to the antigen.

3. The method of claim 1, wherein the protein antigens are anchored physically to the plant spore at an interior surface of the pores.

4. The method of claim 1, wherein the immunogenic composition is adapted to be delivered orally.

5. The method of claim 1, wherein the immunogenic composition is a liquid.

6. The method of claim 1, further comprising a polymer coating applied to the plant spore, wherein the polymer coating is a physical barrier that fills an inner cavity of the spore.

7. The method of claim 6, wherein polymer is a hydrogel.

8. The method of claim 6, wherein antigen is anchored physically to the plant spore.

9. The method of claim 1, further comprising one or more adjuvants disposed on an outer surface of the plant spore, wherein the one or more increase the immune responses in the subject.

10. The method of claim 9 further comprising a polymer coating applied to the plant spore, wherein the polymer coating is a diffusion barrier, a coating that includes physical attachment that coats the exterior of the plant spore.

11. A method of modulating an immune response in a subject comprising the steps of:
    identifying that the subject is in need of immunostimulation;
    providing an immunogenic composition for oral administration comprising an intact or fragment or a combination thereof of a plant spore disposed in a pharmaceutical carrier and a cryoprotectant for delivery to a subject, wherein the plant spore comprises multiple pores; and one or more antigens, wherein the one or more antigens are disposed in an inner cavity of the plant spore or the multiple pores of the plant spore, wherein the one or more protein antigens cause an immune responses in the subject; and
    administering the immunogenic composition to the subject to cause an immune response to the antigen.

12. The method of claim 11, wherein the modulation comprises an increase in the immune response.

13. The method of claim 11, wherein the one or more antigens comprise two or more proteins.

14. The method of claim 11, wherein the immunogenic composition is adapted to be delivered orally.

15. The method of claim 11, wherein the immunogenic composition is a liquid.

16. The method of claim 11, wherein the one or more antigens are physically attached to the plant spore.

17. The method of claim 11, further comprising a polymer coating applied to the plant spore, wherein the polymer coating is a diffusion barrier, a coating that includes physical attachment that coats the exterior of the plant spore.

18. The method of claim 17, wherein polymer is a hydrogel.

19. The method of claim 11, further comprising one or more adjuvants.

20. The method of claim 19, wherein the adjuvant is alum.

21. The method of claim 19, further comprising a polymer coating that is a physical attachment coats the exterior surface of the plant spore.

22. A method of modulating an immune response in a subject comprising the steps of:
   providing the subject with an immunogenic composition adapted for oral administration comprising an intact or fragment or a combination thereof a plant spore disposed in a pharmaceutical carrier and a cryoprotectant for delivery to a subject, wherein the plant spore comprises multiple pores and a protein antigen disposed within an inner surface of the plant spore; and one or more immuno-modulating agents disposed in the composition, wherein the immune-modulating agent maybe disposed on the inner cavity, in the multiple pores, of the plant spore, wherein the one or more immune-modulating agents increase an immune responses in the subject; and
   administering the immunogenic composition to the subject to trigger an immune response specific to the antigen.

23. The method of claim 22, wherein the one or more immune-modulating agents is alum.

24. The method of claim 22, wherein the immunogenic composition is adapted to be delivered orally.

25. The method of claim 22, wherein the immunogenic composition is a liquid.

26. The method of claim 22, wherein the cryoprotectant is trehalose.

27. The method of claim 22, wherein the one or more immune-modulating agents are physically attached to the interior of the plant spore.

28. The method of claim 22, further comprising a polymer coating that includes physical attachment that coats an exterior surface of the plant spore, wherein the polymer coating is a diffusion barrier, a coating that includes physical attachment that coats the exterior of the plant spore.

29. The method of claim 28, wherein polymer is a hydrogel.

30. A method of modulating an immune response in a subject comprising the steps of:
   injecting a composition comprising one or more protein antigens and at least one of an intact or fragment of a plant spore in an amount sufficient to trigger an immune response disposed in a pharmaceutical carrier and a cryoprotectant for delivery to the subject, wherein the plant spore comprises multiple pores and the interior of the pores of the plant spore comprise the protein antigen; and
   administering the composition to the subject to cause an immune response that is specific to the antigen.

31. The method of claim 30, wherein the composition is adapted to be delivered orally.

32. The method of claim 30, further comprising the step of providing the subject with one or more compositions that neutralize gastric acid selected from at least one of before, during or after immunization.

\* \* \* \* \*

UNITED STATES PATENT AND TRADEMARK OFFICE
CERTIFICATE OF CORRECTION

PATENT NO. : 9,782,351 B2
APPLICATION NO. : 14/053091
DATED : October 10, 2017
INVENTOR(S) : Gill et al.

Page 1 of 1

It is certified that error appears in the above-identified patent and that said Letters Patent is hereby corrected as shown below:

In the Specification

On Column 1, Line 24, following "STATEMENT OF FEDERALLY FUNDED RESEARCH": Delete "None," and insert -- This invention was made with government support under HD075691 awarded by the National Institute of Health. The Government therefore has certain rights in the invention. --

Signed and Sealed this
First Day of February, 2022

Drew Hirshfeld
*Performing the Functions and Duties of the*
*Under Secretary of Commerce for Intellectual Property and*
*Director of the United States Patent and Trademark Office*